United States Patent
Nam et al.

(10) Patent No.: US 11,826,282 B2
(45) Date of Patent: Nov. 28, 2023

(54) METHODS AND SYSTEMS FOR CATARACT SURGERY USING INTRAOCULAR ILLUMINATION

(71) Applicant: Oculight Co., Ltd., Seongnam-si (KR)

(72) Inventors: Dong Heun Nam, Seoul (KR); Jinman Kim, Yongin-si (KR); Ki Ho Park, Seoul (KR); Youngsub Eom, Seoul (KR)

(73) Assignee: Oculight Co., Ltd., Seongnam-si (KR)

( * ) Notice: Subject to any disclaimer, the term of this patent is extended or adjusted under 35 U.S.C. 154(b) by 636 days.

(21) Appl. No.: 16/880,356

(22) Filed: May 21, 2020

(65) Prior Publication Data

US 2021/0361480 A1 Nov. 25, 2021

(51) Int. Cl.
*A61F 9/007* (2006.01)
*A61F 9/013* (2006.01)

(52) U.S. Cl.
CPC .......... *A61F 9/00736* (2013.01); *A61F 9/013* (2013.01)

(58) Field of Classification Search
CPC . A61B 9/00; A61B 17/0231; A61B 2090/306; A61B 90/30
See application file for complete search history.

(56) References Cited

U.S. PATENT DOCUMENTS

| | | | | |
|---|---|---|---|---|
| 4,693,245 A | * | 9/1987 | Pao | A61F 9/00736 606/107 |
| 5,928,140 A | * | 7/1999 | Hardten | A61B 17/0231 600/236 |
| 6,592,541 B1 | * | 7/2003 | Kurwa | A61F 9/00745 604/521 |
| 7,704,246 B2 | * | 4/2010 | Connor | A61B 90/30 606/4 |
| 2004/0215065 A1 | * | 10/2004 | Setten | A61B 90/36 600/249 |
| 2005/0245916 A1 | * | 11/2005 | Connor | A61B 90/30 606/4 |
| 2011/0282160 A1 | * | 11/2011 | Bhadri | A61B 17/3423 600/236 |

* cited by examiner

*Primary Examiner* — Darwin P Erezo
*Assistant Examiner* — Brigid K Byrd
(74) *Attorney, Agent, or Firm* — United One Law Group LLC; Kongsik Kim; Jhongwoo Peck

(57) ABSTRACT

A method for cataract surgery includes incising a continuous curvilinear capsulorrhexis (CCC) in an anterior capsule of a lens of an eye, inserting an endoillumination probe into the lens through the CCC, further inserting the endoillumination probe to a location below an equator of the lens and below a nucleus of the lens, tilting the endoillumination probe to laterally aim light emitted from the endoillumination probe behind the nucleus, and chopping the nucleus with a chopper needle of the endoillumination probe. The chopping further includes chopping the nucleus with a phaco tip.

9 Claims, 18 Drawing Sheets

Related Art

METHODS AND SYSTEMS FOR CATARACT SURGERY USING INTRAOCULAR ILLUMINATION

TECHNICAL FIELD

The present disclosure relates to methods and systems for cataract surgery using intraocular illumination, and more particularly, to methods and systems for cataract surgery using an endoillumination probe inserted into anterior chamber of eye.

RELATED ART

Cataract is an ophthalmological condition causing blurry vision due to the clouding of the normally clear lens of the eye. As a means to treat the condition, the cloudy natural lens is replaced with a clear artificial lens through a surgical operation. The cataract surgery involves a removal of the cloudy natural cataract lens by ultrasonic destruction or mechanical chopping. Subsequently, the artificial interocular lens is implanted.

SUMMARY

The present disclosure provides a method and a system for cataract surgery using intraocular illumination. The cataract surgery using intraocular illumination according to the present disclosure may provide improved optical image with optimized color, contrast, and brightness to an operator, and thereby improving the visibility and convenience of the operator. Since the intraocular illumination according to the present disclosure can illuminate light between a nucleus and a posterior capsule of a lens, blind spots or dead zones may be prevented or decreased. Moreover, due to the use of an endoillumination probe, the intraocular illumination according to the present disclosure may reduce discomfort, macular photostress, or retinal phototoxicity of both the patient and the surgeon. As a result, more reliable surgeries may be performed.

According to an aspect of the present disclosure, a method for cataract surgery may include incising a continuous curvilinear capsulorrhexis (CCC) in an anterior capsule of a lens of an eye, inserting an endoillumination probe into the lens through the CCC, further inserting the endoillumination probe to a location below an equator of the lens and below a nucleus of the lens, tilting the endoillumination probe to laterally aim light emitted from the endoillumination probe behind the nucleus, and chopping the nucleus with a chopper needle of the endoillumination probe. Additionally, the chopping may further include chopping the nucleus with a phaco tip.

One or more of the following features may be included individually or in any combinations thereof. The method may further include adjusting illumination parameters of the endoillumination probe. The light illuminated by the endoillumination probe may be white light. The illumination parameters may include one or more selected from the group consisting of an illuminance of the light, an angle of the endoillumination probe with respect to an optical axis of the eye, a depth of insertion of the endoillumination probe, and a location of insertion within the eye. The method may further include determining whether reflected light is observed within predetermined ranges of observed wavelength components in a spectrum and observed intensity, and adjusting the illumination parameters in response to determining that the reflected light is observed without the predetermined ranges. In particular, the illumination parameters may be selected to cause reflected light to appear substantially blue or green light. For example, the illumination parameters may be selected to cause reflected light to include a major wavelength component in a spectrum that is equal to or greater than about 420 nm and equal to or less than about 570 nm. Further, the illuminance of the light may be about 0.1 lux.

According to another aspect of the present disclosure, an endoillumination probe may include a handle including a proximal end and a distal end, a chopper needle that protrudes from the distal end of the handle and includes a linear portion and a bent portion, and an optical cable that penetrates through the handle and the chopper needle.

One or more of the following features may be included individually or in any combinations thereof. The bent portion of the chopper needle may be bent to about 90° with respect to the linear portion of the chopper needle. Further, the handle may include a bent portion, and the bent portion of the handle and the bent portion of the chopper needle may be bent in opposite directions.

According to another aspect of the present disclosure, a system for cataract surgery may include an endoillumination probe configured to be inserted into an anterior chamber of an eye and to illuminate light therein. In particular, illumination parameters of the endoillumination probe may be adjusted to cause a color and an intensity of reflected light to be within predetermined ranges, respectively. The endoillumination probe may include a handle including a proximal end and a distal end, a chopper needle that protrudes from the distal end of the handle and includes a linear portion and a bent portion, and an optical cable that penetrates through the handle and the chopper needle.

One or more of the following features may be included individually or in any combinations thereof. The illumination parameters may include one or more selected from the group consisting of an illuminance of the light, an angle of the endoillumination probe with respect to an optical axis of the eye, and a depth of insertion of the endoillumination probe. The system may further include a photodetector configured to measure at least one of the color or the intensity of the reflected light. Further, a controller configured to adjust the illumination parameters of the endoillumination probe based on measurements by the photodetector may be included. The photodetector may be implemented as an imaging device, and the system may further include a display that displays an image being captured by the imaging device. The controller may be configured to adjust the image being displayed on the display to cause one or more of a color, a brightness, and a contrast of the image to be within predetermined ranges, respectively. An optical filter may be disposed in front of the imaging device to adjust characteristics of the image being captured by the imaging device.

Notably, the present disclosure is not limited to the combination of the elements as listed above and may be assembled in any combination of the elements as described herein. Other aspects of the disclosure are disclosed herein.

BRIEF DESCRIPTION OF THE DRAWINGS

A brief description of each drawing is provided to more sufficiently understand drawings used in the detailed description of the present disclosure.

Figure 1:
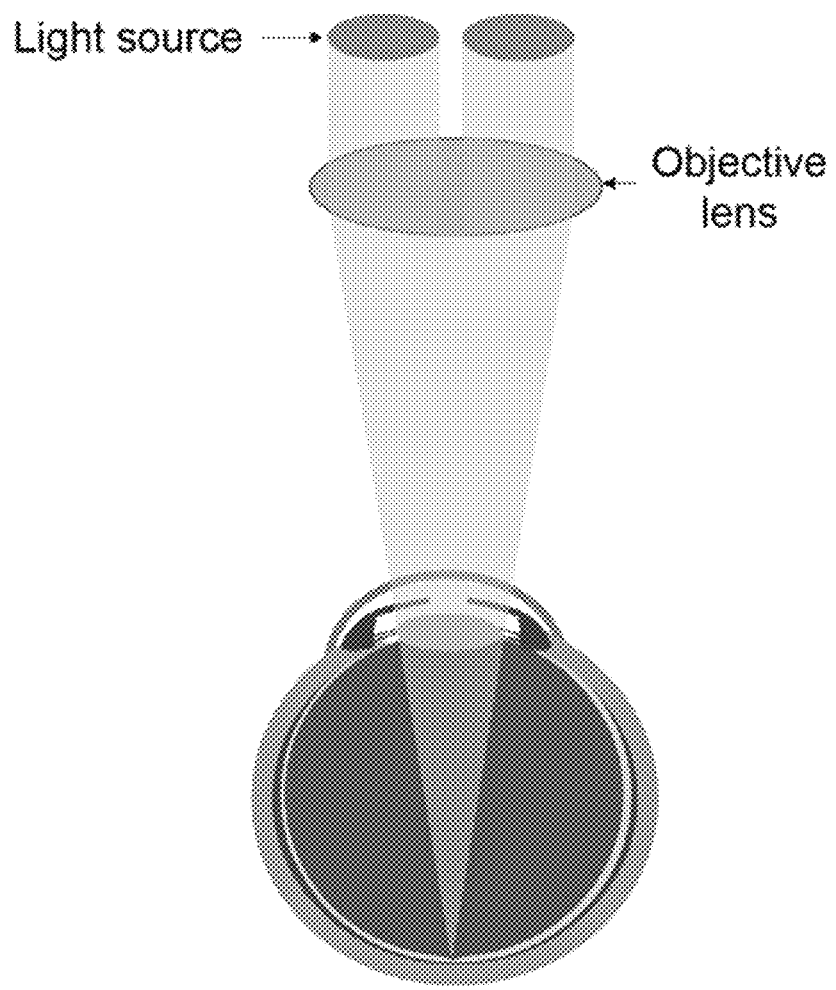
FIG. 1 schematically illustrates microscopic illumination of the related art.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Advantages and features of the present disclosure and a method of achieving the same will become apparent with reference to the accompanying drawings and exemplary embodiments described below in detail. However, the present disclosure is not limited to the exemplary embodiments described herein and may be embodied in variations and modifications. The exemplary embodiments are provided merely to allow one of ordinary skill in the art to understand the scope of the present disclosure, which will be defined by the scope of the claims. Accordingly, in some embodiments, well-known operations of a process, well-known structures, and well-known technologies will not be described in detail to avoid obscure understanding of the present disclosure. Throughout the specification, same reference numerals refer to same elements.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Cataract surgeries are typically performed by an ophthalmic surgeon using an ophthalmic microscope. The ophthalmic microscopes in the related art includes an illumination function. FIG. 1 schematically illustrates microscopic illumination of the related art. As illustrated in FIG. 1, coaxial light is emitted from the microscope, is directed to the eye of the patient, and is reflected forward (e.g., toward a direction of the front of the eye) from the macula. The reflection allows the operator (e.g., a person or a robotic platform performing the cataract surgery) to obtain a view of the surgery. The reflection is observed as a red reflex. Obtaining adequate visibility is considered an important element for a successful cataract surgery. However, in order to obtain sufficient visibility using the coaxial light from the microscope, the illuminance of the coaxial light is required to be set relatively high, which may induce retinal phototoxicity, corneal phototoxicity, or macular photostress. In 1995, the U.S. Food and Drug Administration (FDA) issued a public health advisory concerning retinal photic injuries from using ophthalmic microscopes during cataract surgery.

Figure 2:
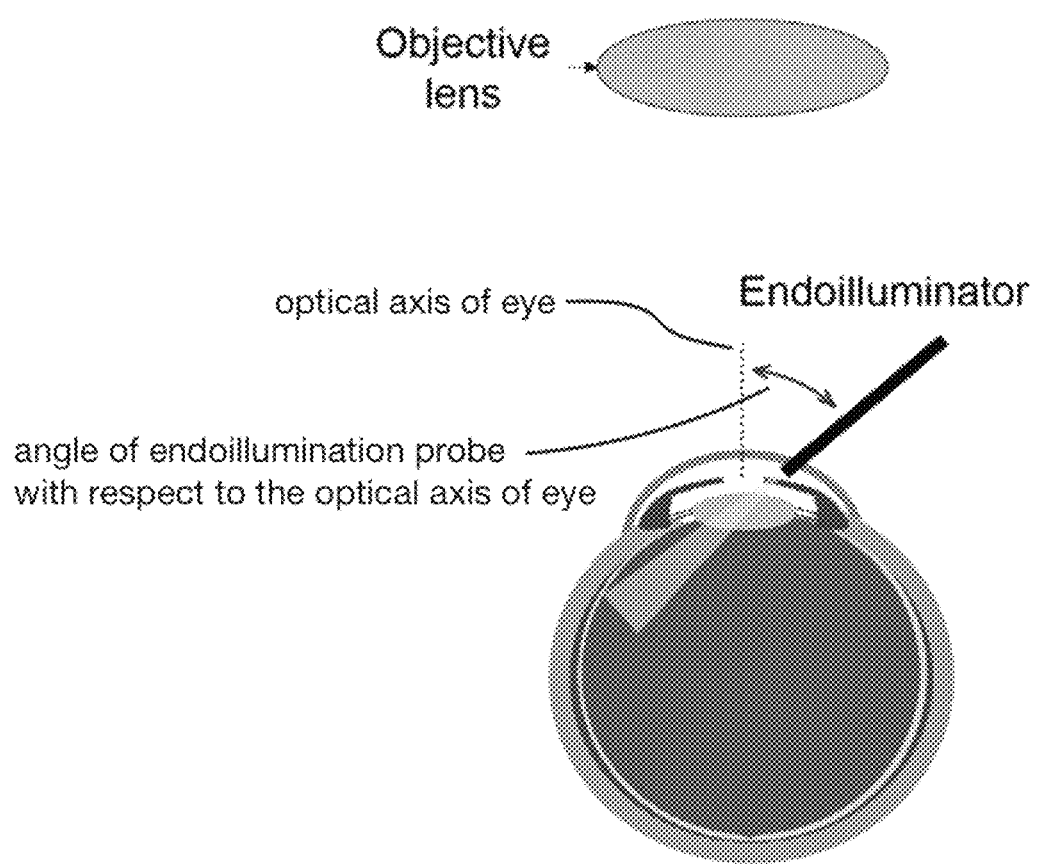
FIG. 2 schematically illustrates intraocular illumination according an exemplary embodiment of the present disclosure.

According to the aspects of the present disclosure, instead of using coaxial light typically produced from the ophthalmic microscope, an endoillumination probe may be inserted through the cornea (limbus) and into the intracameral cavity, for example into an anterior chamber of the eye and within a lens. FIG. 2 schematically illustrates intraocular illumination according an exemplary embodiment of the present disclosure. Using the intraocular illumination, light with an intensity that is less than what is required for the coaxial light may be used and may still provide sufficient illumination for the surgery. As such, a risk of retinal or corneal phototoxicity for the patient may be reduced. In addition, the intraocular illumination may be adjusted to produce a reflection in green or blue light. The green or blue reflection may alleviate strains and/or fatigue to the operator. Moreover, the green or blue reflection may provide improved contrast, sharpness, resolution, and the like, and thereby enhance the visibility even with decreased intensity of the illuminated light. In particular, the intraocular illumination may enable the operator to perceive more details of the lens structures such as the posterior capsule, and may provide improved depth of perception of the intraocular structures. Accordingly, the aspects of the present disclosure may decrease the risk of intraoperative complications, such as retinal or corneal phototoxicity and posterior capsule damage, and increase the success rate of the cataract surgery.

Hereinafter, aspects of the present disclosure will be described with reference to the appended drawings.

Figure 3:
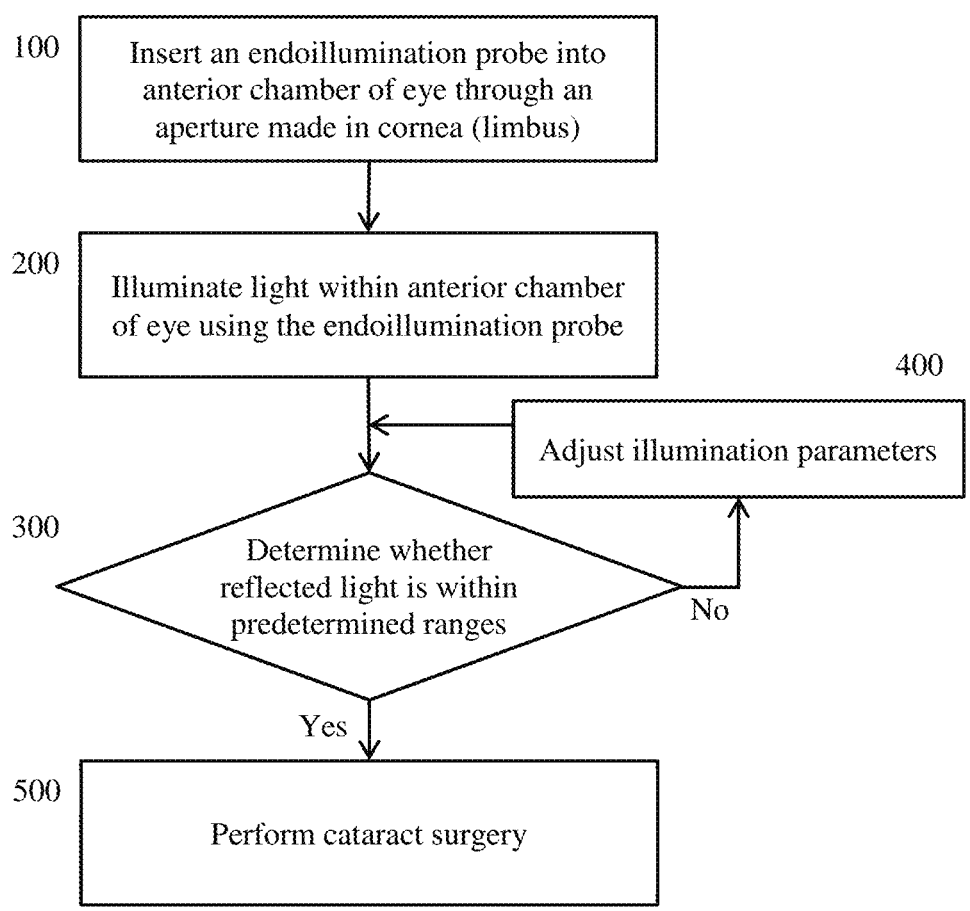
FIG. 3 shows a flow chart for a cataract surgery using intraocular illumination according to an exemplary embodiment of the present disclosure.
Figure 4:
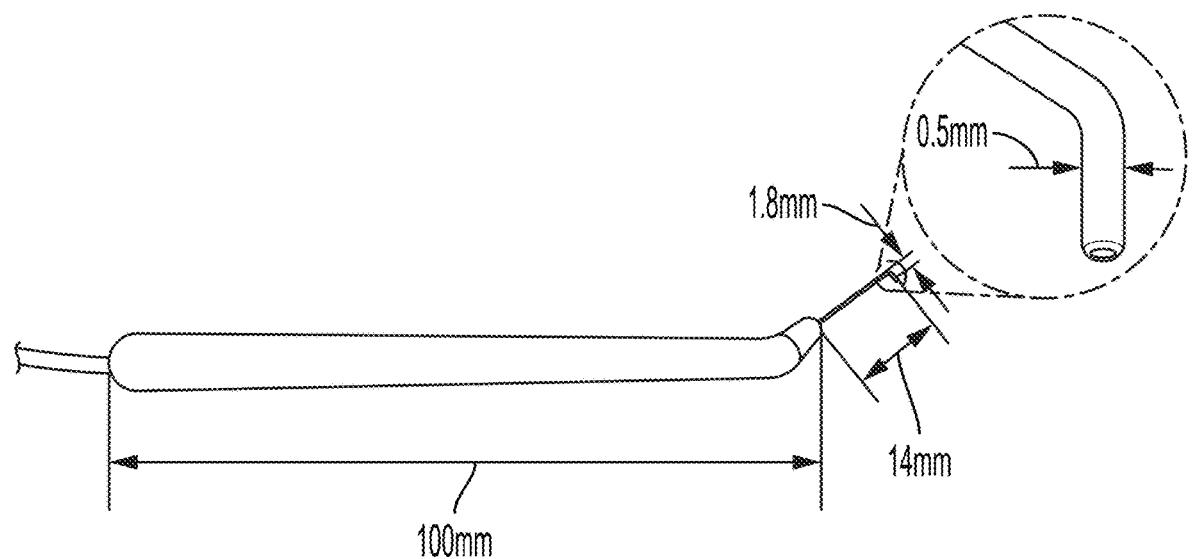
FIG. 4 shows an endoillumination probe for intraocular illumination according to an exemplary embodiment of the present disclosure.

FIG. 3 shows a flow chart for a cataract surgery using intraocular illumination according to an exemplary embodiment of the present disclosure. Referring to FIG. 3, a method for a cataract surgery using intraocular illumination may include a first step 100 of inserting an endoillumination probe into an anterior chamber of an eye. The endoillumination probe that may be employed in the cataract surgery according to the present disclosure will be described in more detail below. In order to insert the endoillumination probe into the anterior chamber of the eye, an aperture may be surgically created through the cornea, and more particularly through the limbus. The location and the dimension of the aperture may be determined based on the dimensions of the endoillumination probe and the area of surgery, and an incision of less than about 1 mm may be made.

In step 200, light having particular illumination parameters may be illuminated within the anterior chamber of the eye using the inserted endoillumination probe. The illumination parameters may include, but are not limited to, an illuminance of the light (i.e., light intensity), an angle of the illumination probe with respect to an optical axis of the eye (see FIG. 2), a depth of insertion of the illumination probe, a location within the lens structure, and the like. The light emitted from the endoillumination probe may be white light, which is a combination of lights of various wavelengths. However, the present disclosure is not limited thereto, and the color of the emitted light may be varied using filters.

In step 300, the operator may determine whether the characteristics of the observed reflection is within predetermined ranges in terms of observed wavelength components in the spectrum and/or observed intensity of the reflection. Here, the reflection may be observed along an optical axis of the eye. In response to determining that the conditions of the observed reflection fails to be within the predetermined ranges, the operator may adjust the illumination parameters (step 400). Conversely, in response to determining that the conditions of the observed reflection falls within the predetermined ranges, the operator may proceed with performing the cataract surgery (step 500).

In particular, the illumination parameters may be selected and adjusted to cause the observed reflection to appear substantially green light or blue light. In some implementations, the illumination parameters may be selected and adjusted to cause the observed reflection to appear substantially green. For example, a major wavelength component in the spectrum of the reflected light may be equal to or greater than about 420 nm and equal to or less than about 570 nm. In some implementations, the major wavelength component of the reflected light may be equal to or greater than about 450 nm and equal to or less than about 570 nm. In some implementations, the major wavelength component of the reflected light may be equal to or greater than about 520 nm and equal to or less than about 560 nm. When the wavelengths of the reflected light when observed along the optical axis of the eye is within these ranges, the reflected light may be observed by the operator as substantially green or blue, and accordingly, may provide improved visibility of the surgery scene and cause less strains or fatigue to the operator's eyes.

Further, the average illuminance of the light that is observed by the operator or detected at a location corresponding to the operator's eyes may be equal to or greater than about 0.01 lux and equal to or less than about 1 lux. In some implementations, the average illuminance of the emitted light may be equal to or greater than about 0.05 lux and equal to or less than about 0.2 lux. In some implementations, the average illuminance of the emitted light may be about 0.1 lux. In terms of the average total spectral irradiance ($\mu W/cm^2$), a illuminance of 0.1 lux may correspond to a total spectral irradiance of about 0.03 $\mu W/cm^2$. It should be noted that, in order to offer sufficient visibility, the required illuminance of the light to be observed by the operator using the endoillumination probe according to the present disclosure is significantly less than the illuminance of the light required using a typical microscope of the related art, which requires about 1.5 to 2.5 lux. Due to the lower intensity of the light illuminated to the macula and cornea, the cataract surgery using interocular illumination according to the present disclosure poses less risk of negatively affecting the retina (macula) and cornea while being able to provide improved visibility.

Figure 5:
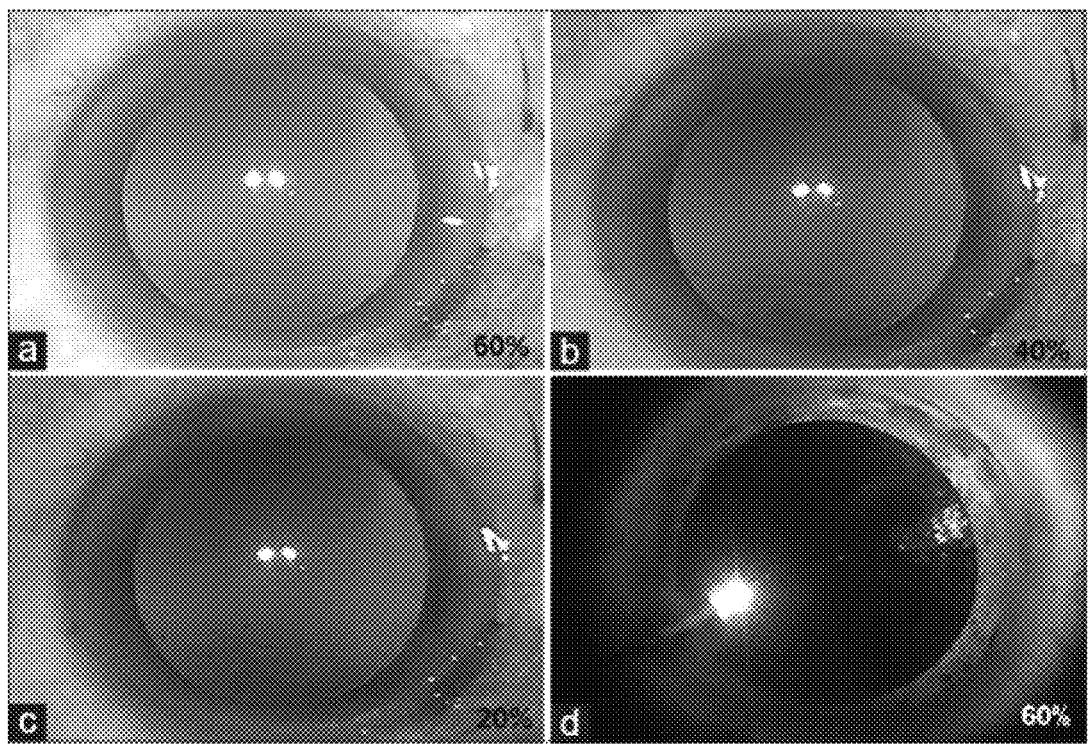
FIG. 5 compares observed reflections using microscope illumination (a), (b), and (c) with various intensities and intraocular illumination according to an exemplary embodiment of the present disclosure.

FIG. 5 shows photographs taken during cataract surgeries at a pause after lens capsule polishing with operating room lights off. FIG. 5 compares the observed reflections using microscope illumination with various intensities and intraocular illumination according to an exemplary embodiment of the present disclosure. Panel (a) of FIG. 5 shows a result using microscope illumination with 60% intensity, which corresponds to about 1.46 lux. The 60% intensity is deemed to provide adequate illumination. Panel (b) of FIG. 5 shows a result using microscope illumination with 40% intensity, corresponding to about 0.66 lux, which offers fair illumination. Panel (c) of FIG. 5 shows a result using microscope illumination with 20% intensity, corresponding to about 0.27 lux, which yields poor illumination. Panel (d) of FIG. 5 shows intraocular illumination using an endoillumination probe with 60% intensity. At 60% intensity of the endoillumination probe, the illuminance corresponds to about 0.1 lux, which is still less than the illuminance of 20% intensity of the microscope illumination. As shown in panel (d) of FIG. 5, the intraocular illumination provides good visibility of the surgery site with improved contrast, sharpness, and resolution as well as a more detailed rendition of the lens structure. Panel (d) of FIG. 5 also shows the reflected light being observed as green light.

Figure 6:
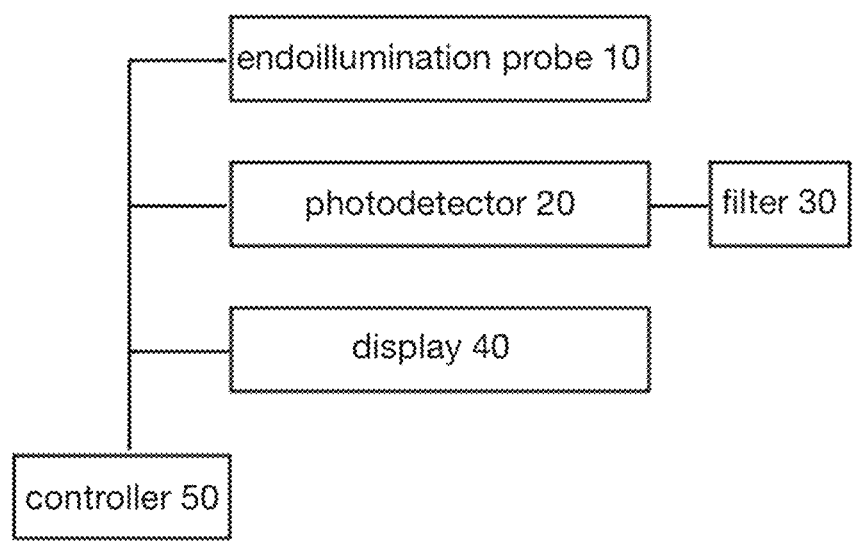
FIG. 6 schematically illustrates a system for cataract surgery using intraocular illumination according to an exemplary embodiment of the present disclosure.

Another aspect of the present disclosure provides a system for a cataract surgery using intraocular illumination. FIG. 6 schematically illustrates a system for cataract surgery using intraocular illumination according to an exemplary embodiment of the present disclosure. Referring to FIG. 6, the system for a cataract surgery using intraocular illumination according to an exemplary embodiment of the present disclosure may include an endoillumination probe 10, a photodetector 20, and a controller 50. The endoillumination probe 10 may be inserted into an anterior chamber of an eye and may illuminate light therein. In particular, illumination parameters of the endoillumination probe 10 may be adjusted to cause observed reflected light to satisfy predetermined conditions. For example, the illumination parameters may include an illuminance of the light, an angle of the endoillumination probe 10 with respect to an optical axis of the eye, a depth of insertion of the endoillumination probe 10 into the anterior chamber, a location of the endoillumination probe 10 within the lens structures, and the like. The photodetector 20 may detect the reflected light and measure at least one of a color or an intensity of the reflected light. Subsequently, the controller 50 may be configured to adjust the illumination parameters of the endoillumination probe 10 based on the measurements by the photodetector 20.

The type of photodetectors that may be used in the system according to an exemplary embodiment of the present disclosure are not particularly limited, and any types of photodetectors that can measure the color and/or the intensity of the reflected light may be implemented. For example, photomultiplier tubes, photodiodes, photoresistors, charge-coupled devices (CCD), complementary metal-oxide semiconductor (CMOS) image sensors, or the like may be employed as the photodetector.

In particular, the photodetector 20 may be implemented as an imaging device (e.g., a camera), and a display 40 may be further included in the system. The display 40 may display an image being captured by the imaging device. The controller 50 may be configured to adjust the image being displayed on the display 40 to cause the color, brightness, and/or contrast of the image to be within predetermined ranges, respectively. In addition, an optical filter 30 may be disposed in front of the imaging device to adjust characteristics of the image being captured by the imaging device, for example, to adjust the color, brightness, and/or contrast of the captured image. The controller 50 may be further configured to adjust one or more of the illumination parameters, the display parameters, and the filter parameters to optimize the visibility for the cataract surgery using intraocular illumination according to the present disclosure. To optimize the parameters, the controller 50 may utilize machine learning algorithms, deep learning algorithms, artificial intelligence (AI) algorithms, or the like to establish correlations between the parameters such as the illuminance, the angle of the endoillumination probe, the depth and location of insertion, and the like.

Additionally or alternatively, the controlling of the illumination parameters may be performed manually by the operator. In such case, the operator may adjust the illuminance, the angle of the endoillumination probe, the insertion depth of the endoillumination probe, the location of the insertion within the lens structures, or the like based on the reflected light that is observed by the operator. The operator may observe the reflected light with own eyes or through the display.

The controller 50 may be implemented as a microprocessor such as a general purpose microprocessor that can be configured to execute program instructions stored in a non-transitory computer readable media. Control logic of the present disclosure may be embodied as non-transitory computer readable media on a computer readable medium containing executable program instructions executed by a processor, controller, control unit, or the like. Examples of the computer readable media include, but are not limited to, ROM, RAM, compact disc (CD)-ROMs, magnetic tapes, floppy disks, hard disks, flash drives, universal serial bus (USB) drives, solid-state drives (SSD), smart cards, and optical data storage devices. The computer readable recording medium can also be distributed in network coupled computer systems so that the computer readable media is stored and executed in a distributed fashion, e.g., by a telematics server or a controller area network (CAN).

Figure 7:
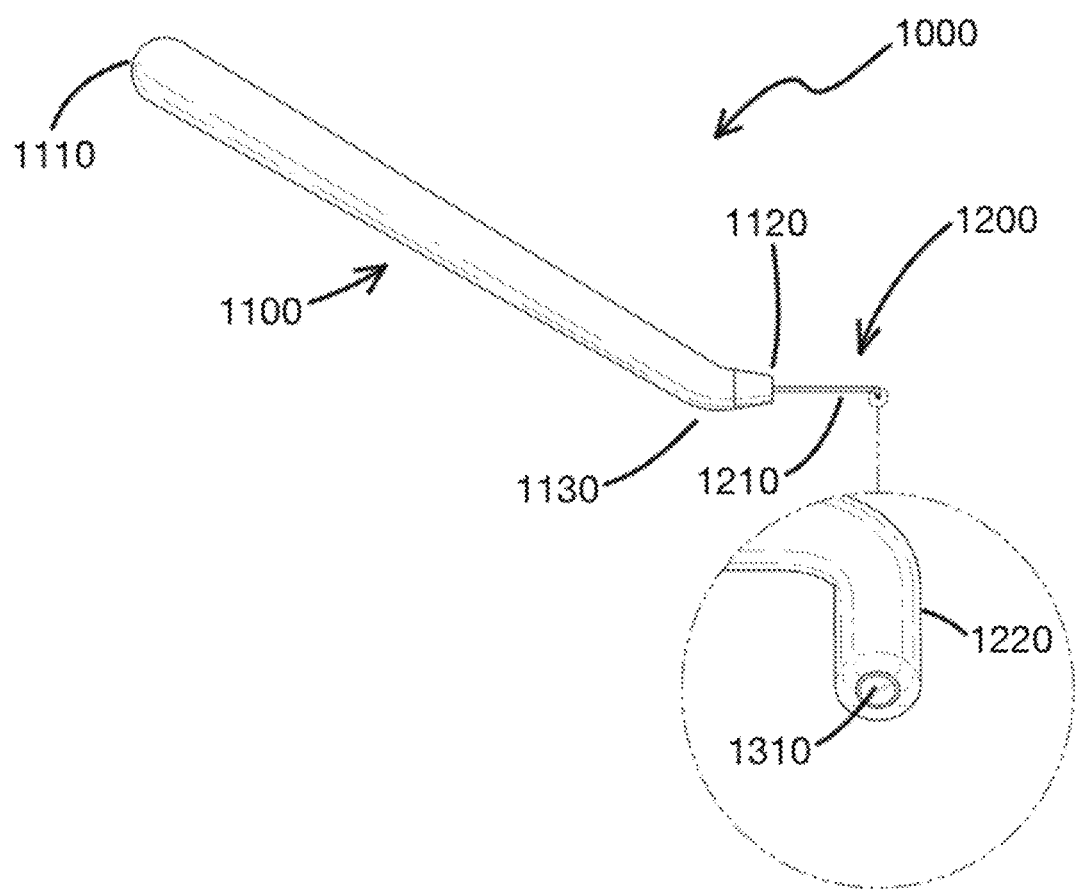
FIGS. 7 and 8 illustrate an endoillumination probe according to an exemplary embodiment of the present disclosure.
Figure 8:
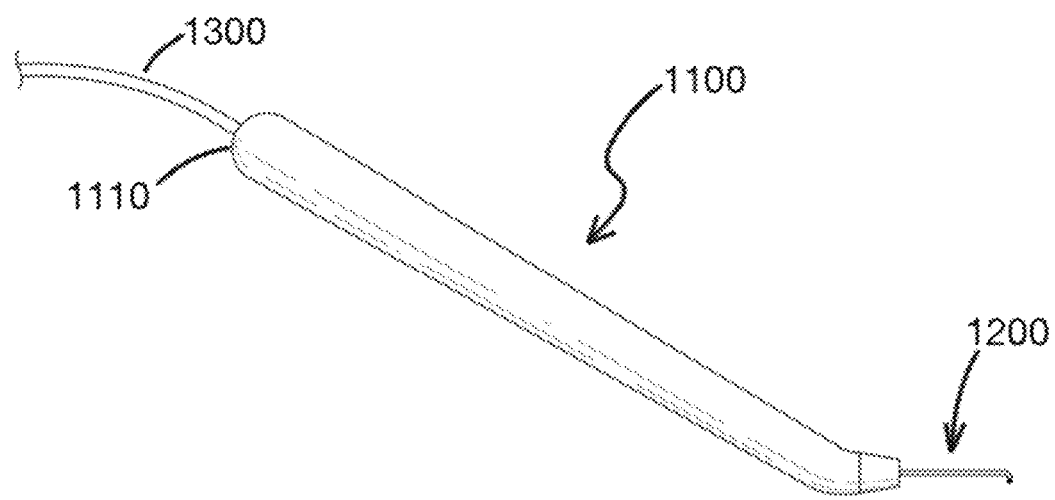

Another aspect of the present disclosure provides an endoillumination probe for providing intraocular illumination during cataract surgery or as a part of an intraocular illumination system for cataract surgery. FIGS. 7 and 8 illustrate an endoillumination probe according to an exemplary embodiment of the present disclosure. Referring to FIG. 7, the endoillumination probe 1000 for cataract surgery may include a handle 1100 and a chopper needle 1200. The handle 1100 may include a proximal end 1110 and a distal end 1120. The chopper needle 1200 may protrude from the distal end 1120 of the handle 1100. In particular, the chopper needle 1200 may include a linear portion 1210 and a bent portion 1220 formed at a distal end of the linear portion 1210. The linear portion 1210 and the bent portion 1220 may form an angle with respect to each other that is equal to or greater than about 60° and equal to or less than about 120°. In some implementations, the angle between the linear portion 1210 and the bent portion 1220 of the chopper needle 1200 may be about 90°. A length of the bent portion 1220 may be equal to or greater than about 1 mm and equal to or less than about 2.5 mm. In some implementations, the length of the bent portion 1220 of the chopper needle 1200 may be about 1.8 mm. Due to the bent portion 1210, the endoillumination probe 1000 according to an exemplary embodiment of the present disclosure may allow the light beam emitted therefrom to be steered more effectively within the lens structure during the surgery.

The handle 1100 may include a bent portion 1130 to provide a better holding angle during the surgery. The bent portion 1130 of the handle 1100 and the bent portion 1220 of the chopper needle 1200 may be bent in opposite directions. For example, as shown in FIG. 7, the bent portion 1130 of the handle 1100 may be bent upward ("upward" being as indicated in FIG. 7), and the bent portion 1220 of the chopper needle 1200 may be bent downward ("downward" being as indicated in FIG. 7).

Referring to FIG. 8, the endoillumination probe 1000 according to an exemplary embodiment of the present disclosure may further include an optical cable 1300 attached to the proximal end 1110 of the handle 1100. The optical cable 1300 may include a sheath and a core. In particular, the core of the optical cable 1300 may extend through both the handle 1100 and the chopper needle 1200 such that an terminal end 1310 (shown in FIG. 7) of the core is exposed at the distal end of the chopper needle 1200. The optical cable 1300 may transmit light therethrough. Another end of the optical cable 1300 that is not shown in FIG. 8 may be coupled to a light source or a power supply that generates the light to be transmitted through the optical cable and be emitted via the terminal end 1310 of the optical cable 1300.

The handle 1100 of the endoillumination probe 1000 may be made of a plastic or polymer material. However, the material of the handle 1100 is not limited thereto, and various other materials may be used. The chopper needle 1200 of the endoillumination probe 1000 may be made of stainless steels or titanium alloys. For example, the chopper needle 1200 may be made of a medical-grade stainless steel (e.g., SAE 315 or SAE 315L stainless steels). However, the material of the chopper needle 1200 is not limited thereto, and any other bio-compatible materials may be used.

Figure 9:
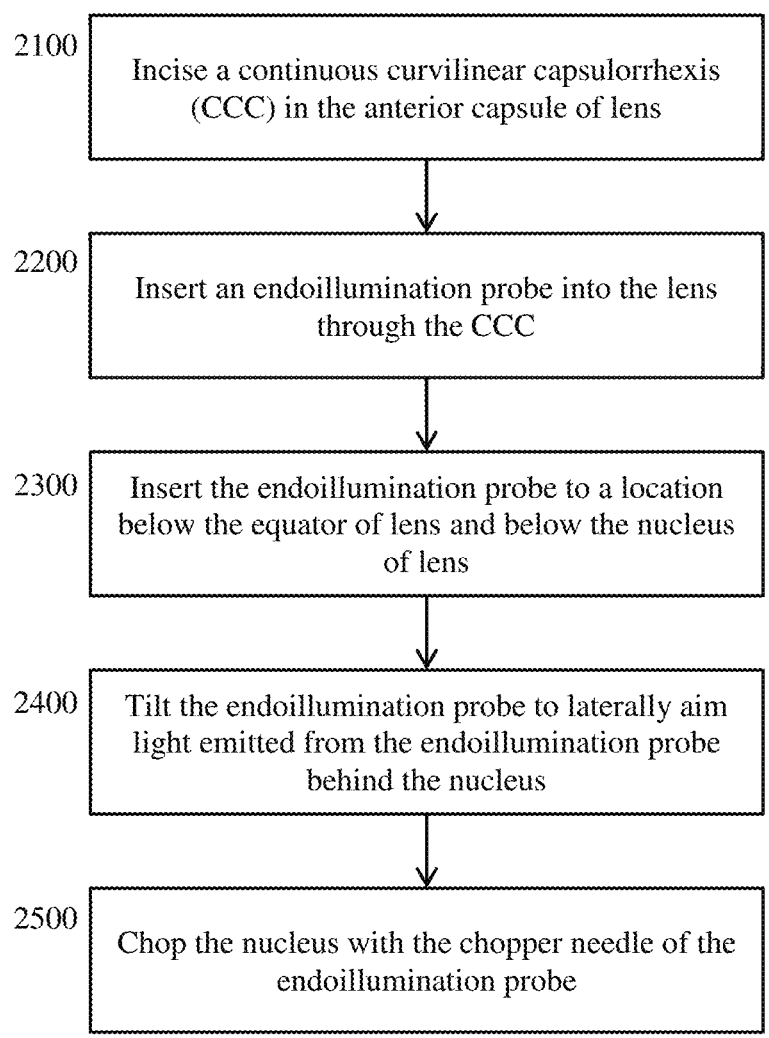
FIG. 9 shows a flow chart for a method for chopping a lens nucleus using an endoillumination probe according to an exemplary embodiment of the present disclosure.

Hereinbelow, a method of cataract surgery using an endoillumination probe according to the present disclosure will be described with reference to FIGS. 9, 10A-10E, and 11A-11D. FIG. 9 shows a flow chart for a method for chopping a lens nucleus using an endoillumination probe according to the present disclosure, and FIGS. 10A-10E illustrate the steps of the method. FIGS. 11A-11D show images taken during the cataract surgery using intraocular illumination according to the present disclosure.

Figure 10A:
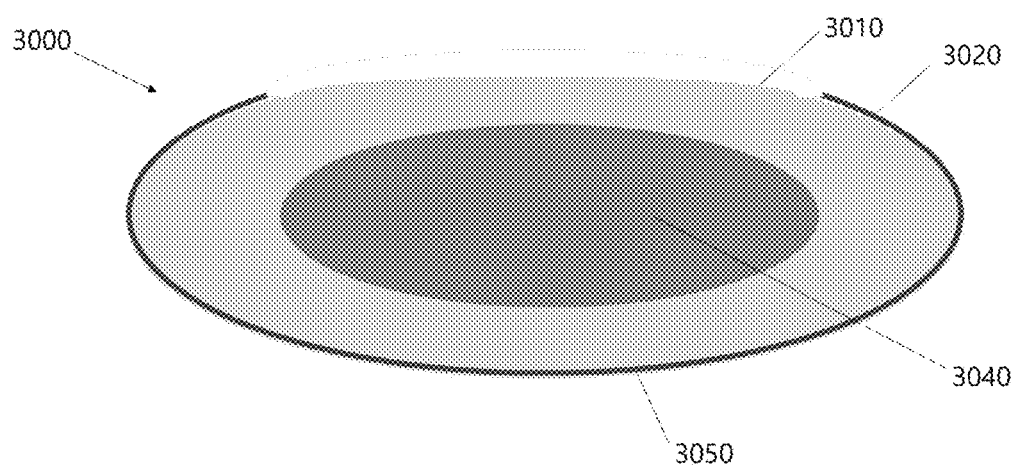
FIGS. 10A-10E illustrate the steps of a method for chopping a lens nucleus according to the present disclosure.
Figure 10B:
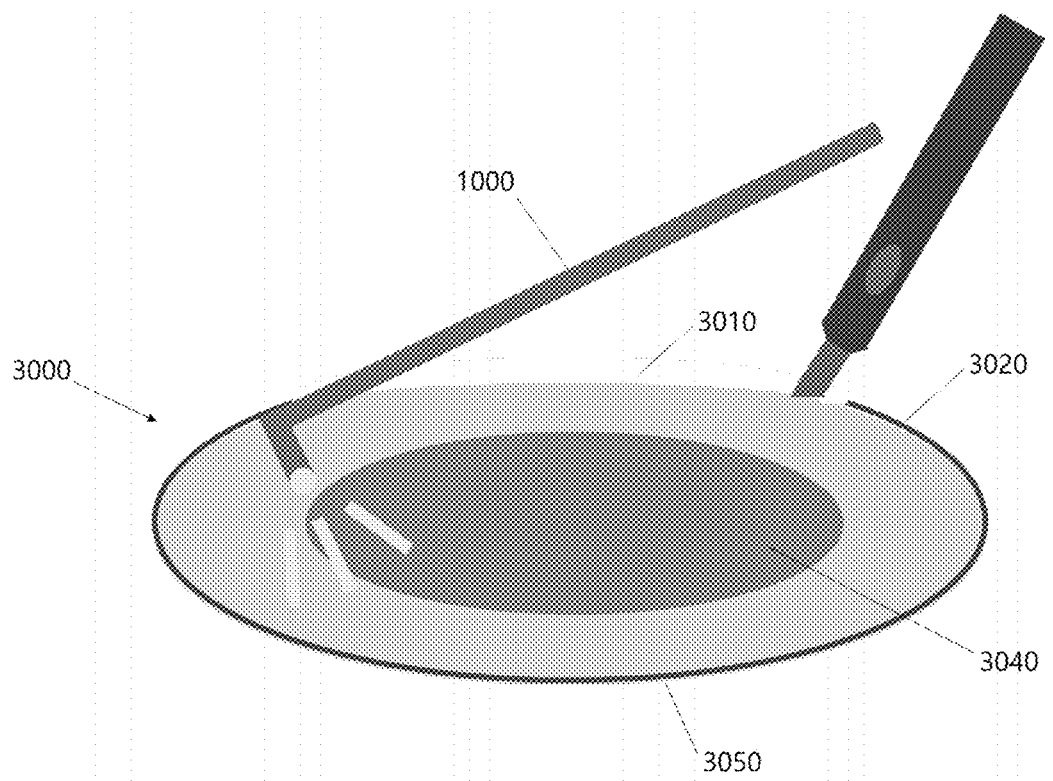
Figure 10C:
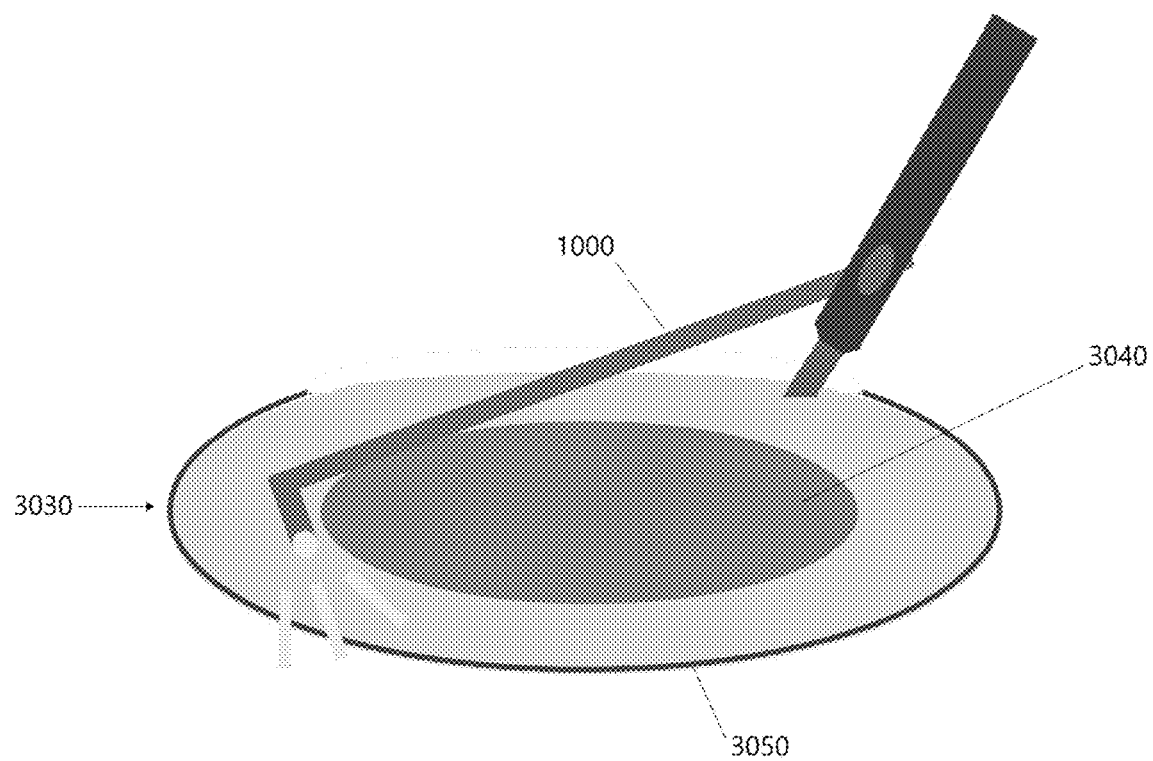
Figure 11A:
FIGS. 11A-11D show images taken during the cataract surgery using intraocular illumination according to the present disclosure.
Figure 11A:
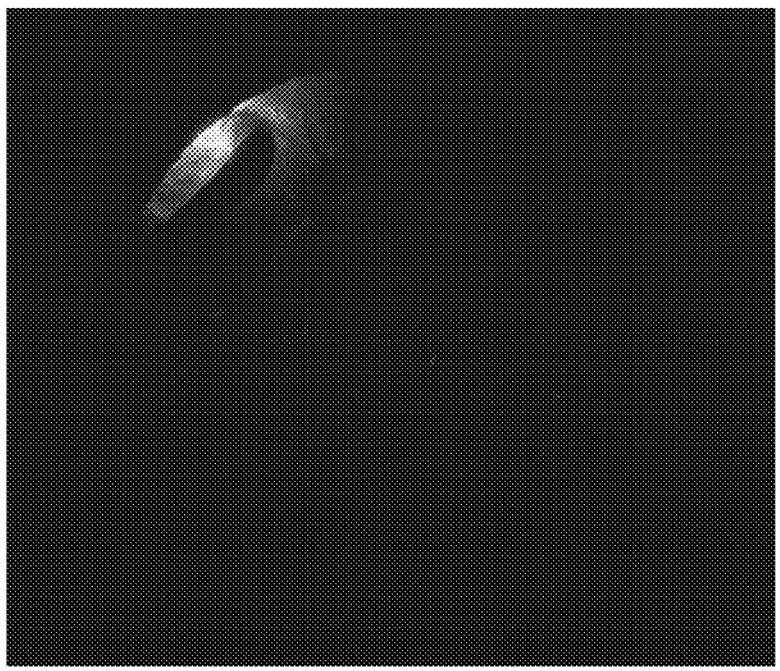
Figure 11B:
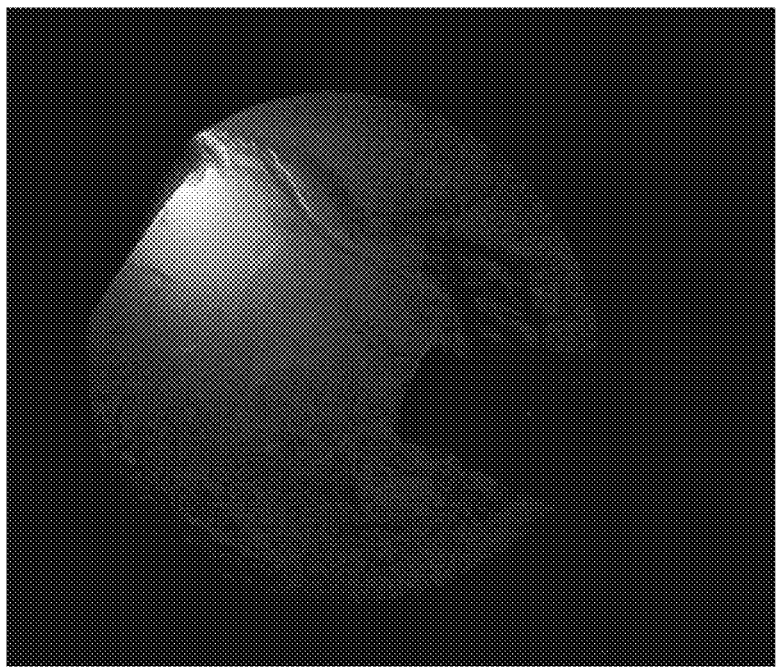
Figure 11B:
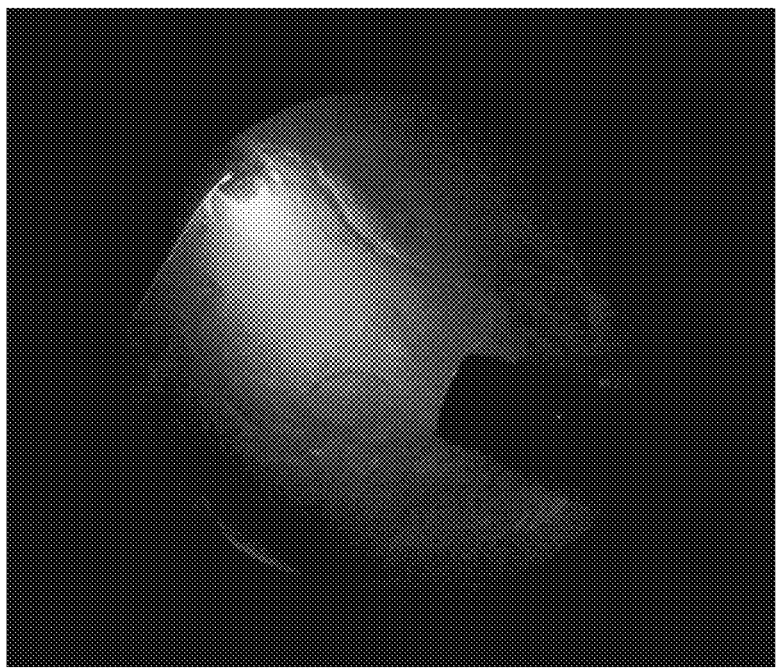
Figure 11C:
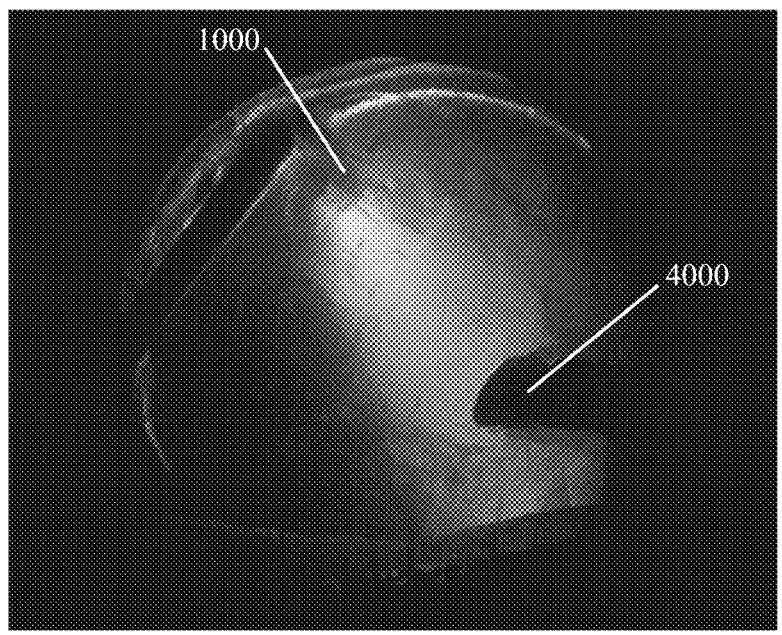
Figure 11C:
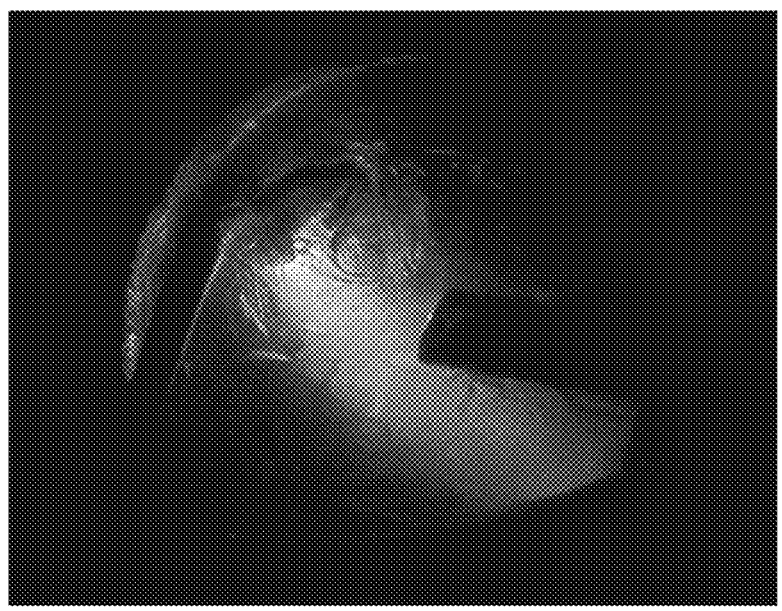

In step 2100, after making an incision through the limbus region of the cornea, a continuous curvilinear capsulorrhexis (CCC) 3010 may be opened in the anterior capsule 3020 of the lens 3000 as shown in FIG. 10A. In step 2200, as shown in FIG. 10B, the endoillumination probe 1000 may be inserted through the CCC 3010 into the lens 3000. FIG. 11A shows an image when the endoillumination probe 1000 is inserted within the lens. In step 2300, as shown in FIG. 10C, the endoillumination probe 1000 may be further inserted to a location below the equator 3030 and below the nucleus 3040 of the lens 3000. When the endoillumination probe 1000 emits light below the equator 3030, as shown in FIG. 11B, the light can illuminate the posterior capsule 3050 behind the nucleus 3040 more effectively, and thereby decrease the risk of damaging the posterior capsule 3050 of the lens 3000 during the surgery. The posterior capsule damage is one of major concerns during the cataract surgery.

Figure 10D:
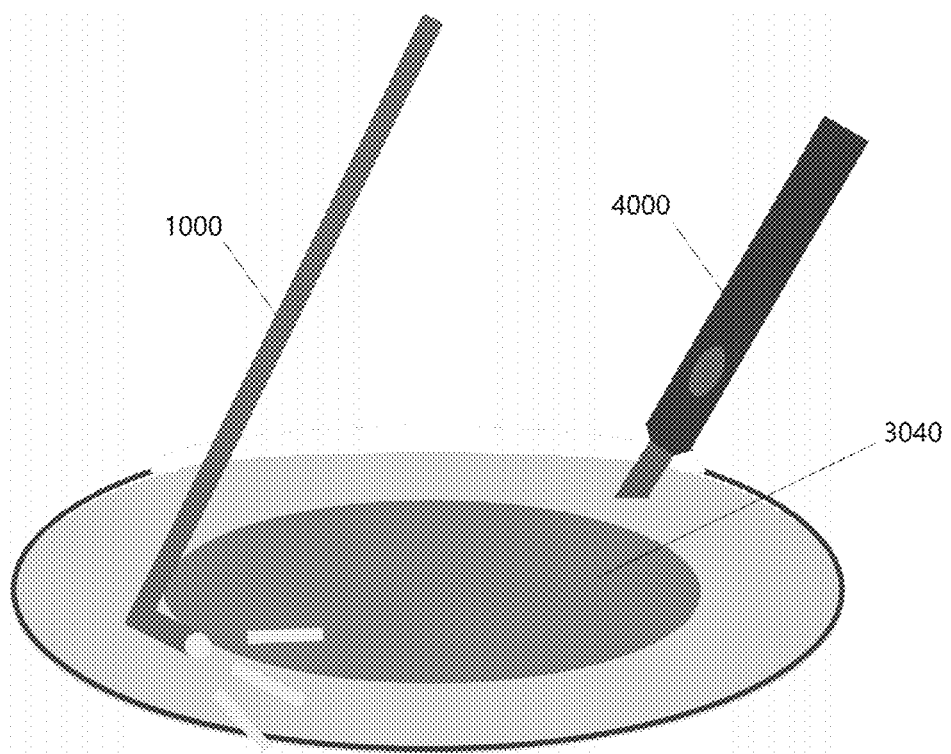
Figure 10E:
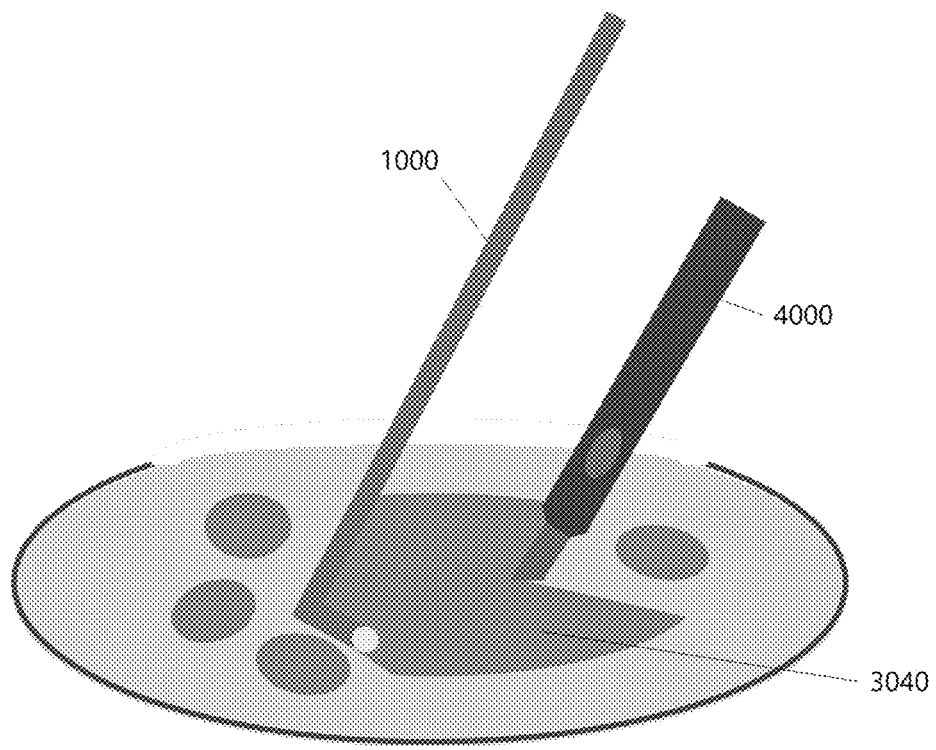
Figure 11D:
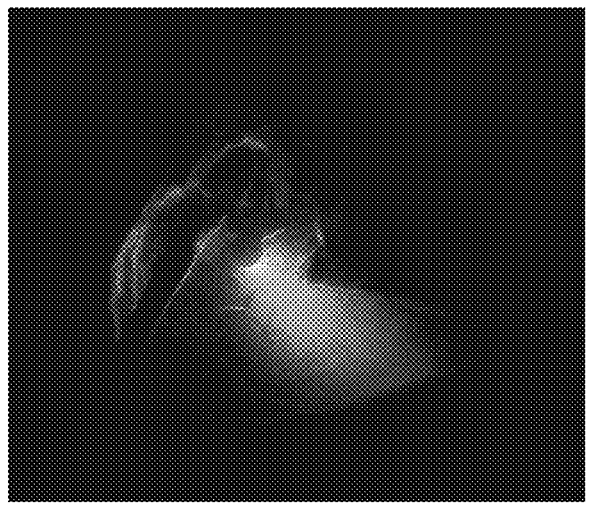
Figure 11D:
Figure 11D:

Subsequently, in step 2400, the endoillumination probe 1000 may be tilted to cause the light emitted from the tip thereof to be more laterally directed, as shown in FIG. 10D. Here, due to the bent portion of the chopper needle, the light may illuminate the posterior space of the nucleus 3040. The light may be steered to illuminate toward a phaco tip 4000 for chopping the nucleus 3040 of the lens 3000. The images shown in FIG. 11C indicate that the light from the endoillumination probe 1000 can provide a light path toward the phaco tip 4000 between the nucleus 3040 and the posterior capsule 3050, and sufficient visibility of the lens structure can be achieved. In step 2500, as shown in FIG. 10E, the nucleus 3040 may be chopped with the phaco tip 4000. In addition, the chopper needle of the endoillumination probe 1000 may be used along with the phaco tip 4000 in chopping the nucleus 3040 as shown in FIG. 11D.

As set forth herein, the subject matter of the present disclosure provides a method and a system for cataract surgery using intraocular illumination. By illuminating light within the lens structure between the lens nucleus and the posterior capsule and adjusting illumination parameters of the endoillumination probe to obtain green or blue reflection, the visibility may be improved due to improved contrast, sharpness, resolution, depth of perception, and the like. In particular, the intraocular illumination may enhance the 3-dimensional details of the intraocular structures for an improved visualization during the surgery. The intraocular illumination according to the present disclosure requires less intensity of the illuminated light compared to the microscope illumination of the related art. Therefore, the risk of retinal/corneal phototoxicity and eye strain or fatigue of the operator may be reduced. In addition, due to a chopping needle including a bent portion, the endoillumination probe may be used for both illumination and chopping purposes while the light may be steered more effectively.

Hereinabove, although the present disclosure is described by specific matters such as concrete components, and the like, the exemplary embodiments and the drawings are provided merely for assisting in the entire understanding of the present disclosure. Therefore, the present disclosure is not limited to the exemplary embodiments described herein. Various modifications and changes can be made by a person of ordinary skill in the art to which the present disclosure pertains. The spirit of the present disclosure should not be limited to the above-described exemplary embodiments, and the following claims as well as all technical spirits modified equally or equivalently to the claims should be interpreted to fall within the scope and spirit of the disclosure.

What is claimed is:

1. A method comprising:
    incising a continuous curvilinear capsulorrhexis (CCC) in an anterior capsule of a lens of an eye;
    inserting an endoillumination probe into the lens through the CCC;
    further inserting the endoillumination probe to a location below an equator of the lens and below a nucleus of the lens, thereby illuminating light behind the nucleus of the lens;
    tilting the endoillumination probe to laterally aim the light emitted from the endoillumination probe behind the nucleus; and
    chopping the nucleus with a chopper needle of the endoillumination probe.

2. The method of claim 1, wherein the chopping further includes chopping the nucleus with a phaco tip.

3. The method of claim 1, further comprising:
    adjusting illumination parameters of the endoillumination probe.

4. The method of claim 3, wherein the light illuminated by the endoillumination probe is white light.

5. The method of claim 3, wherein the illumination parameters include one or more selected from the group consisting of an illuminance of the light, an angle of the endoillumination probe with respect to an optical axis of the eye, a depth of insertion of the endoillumination probe, and a location of insertion within the eye.

6. The method of claim 5, wherein the illuminance of the light is about 0.1 lux.

7. The method of claim 3, further comprising:
    determining whether reflected light is observed within predetermined ranges of observed wavelength components in a spectrum and observed intensity; and
    adjusting the illumination parameters in response to determining that the reflected light is observed without the predetermined ranges.

8. The method of claim 3, wherein the illumination parameters are selected to cause reflected light to appear substantially blue or green light.

9. The method of claim 3, wherein the illumination parameters are selected to cause reflected light to include a major wavelength component in a spectrum that is equal to or greater than about 420 nm and equal to or less than about 570 nm.

* * * * *